United States Patent [19]

Vaillancourt

[11] Patent Number: 4,834,108
[45] Date of Patent: May 30, 1989

[54] BLOCKING FILTER TO PREVENT AIR FLOW INTO A FLUID CONDUIT TO A TRANSDUCER

[75] Inventor: Vincent L. Vaillancourt, Livingston, N.J.

[73] Assignee: Manresa, Inc., Hillsdale, N.J.

[21] Appl. No.: 872,151

[22] Filed: Jun. 9, 1986

[51] Int. Cl.$^4$ ............................................... A61B 5/02
[52] U.S. Cl. .................................. 128/673; 128/748; 604/126
[58] Field of Search .............................. 128/672–675, 128/748; 604/122, 126, 190

[56] References Cited

U.S. PATENT DOCUMENTS

| | | | |
|---|---|---|---|
| 3,581,733 | 6/1971 | Grandjean | 128/673 |
| 3,675,891 | 7/1972 | Reynolds et al. | 128/673 X |
| 4,252,126 | 2/1981 | Mandl | 128/673 |
| 4,298,358 | 11/1981 | Ruschke | 604/126 X |
| 4,342,218 | 8/1982 | Fox | 128/673 X |
| 4,391,599 | 7/1983 | Jenkins | 604/126 X |
| 4,395,260 | 7/1983 | Todd et al. | 604/122 |
| 4,431,009 | 2/1984 | Marino, Jr. et al. | 128/673 |
| 4,444,198 | 4/1984 | Petre | 128/673 |
| 4,545,389 | 10/1985 | Schaberg et al. | 128/675 X |
| 4,557,269 | 12/1985 | Reynolds et al. | 128/675 |
| 4,571,244 | 2/1986 | Knighton | 128/672 X |

Primary Examiner—Kyle L. Howell
Assistant Examiner—Angela D. Sykes
Attorney, Agent, or Firm—Kenyon & Kenyon

[57] ABSTRACT

This invention is shown with two modes of construction and use. In the first arrangement, there is provided a dual tubular fluid conductor in which the blocking filter is positioned at the entering end of a second fluid conduit leading from a catheter to a transducer. In the second arrangement, the blocking filter is disposed at the fast-flush device and insures an absence of bubbles in a fluid conductor from the device to a transducer. The blocking filter is positioned so as to be in the fluid-conducting path from the patient to a transducer, with this blocking filter of hydrophilic material so that pulse signals sent to and through the fluid conductor connected to the transducer ar not distorted by the presence of air bubbles.

9 Claims, 2 Drawing Sheets

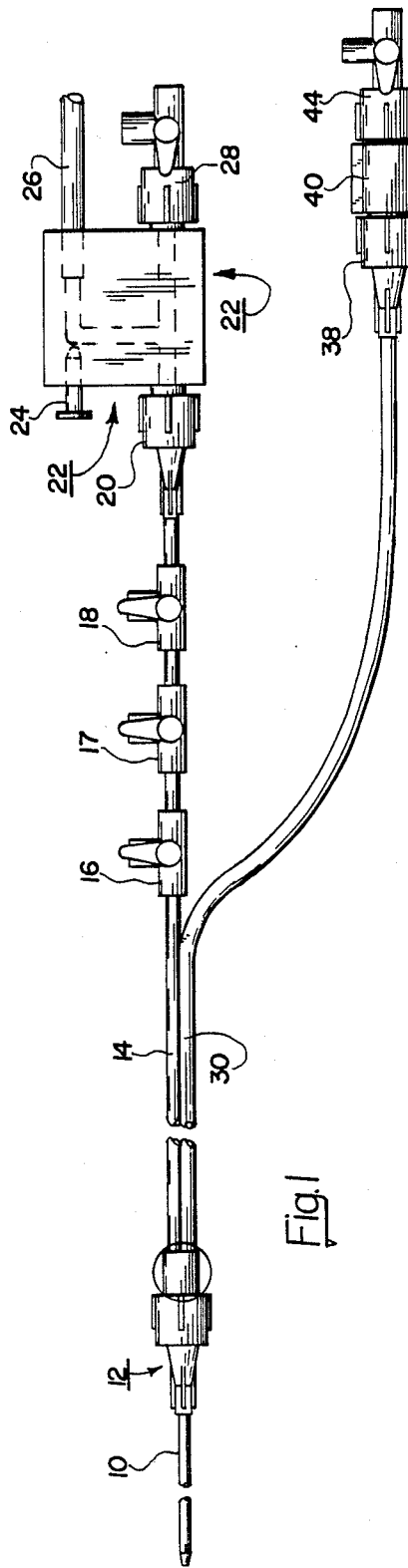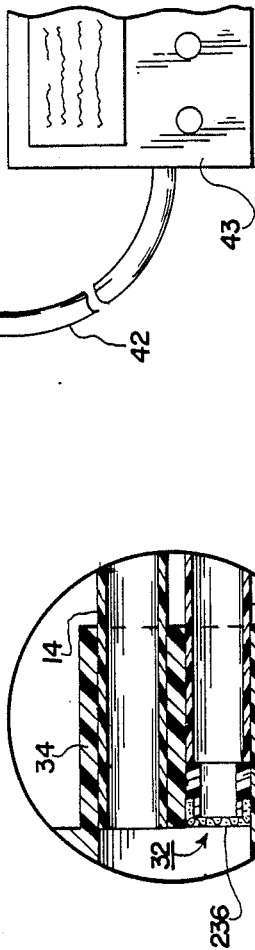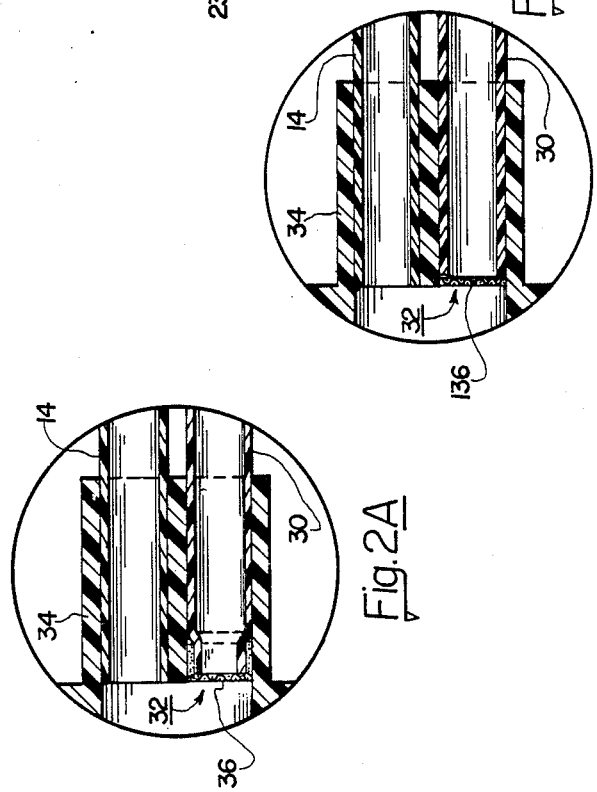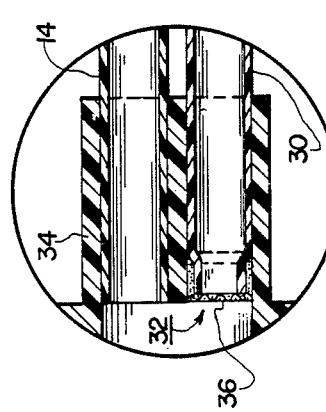
Fig.1
Fig.2A
Fig.2B
Fig.2C

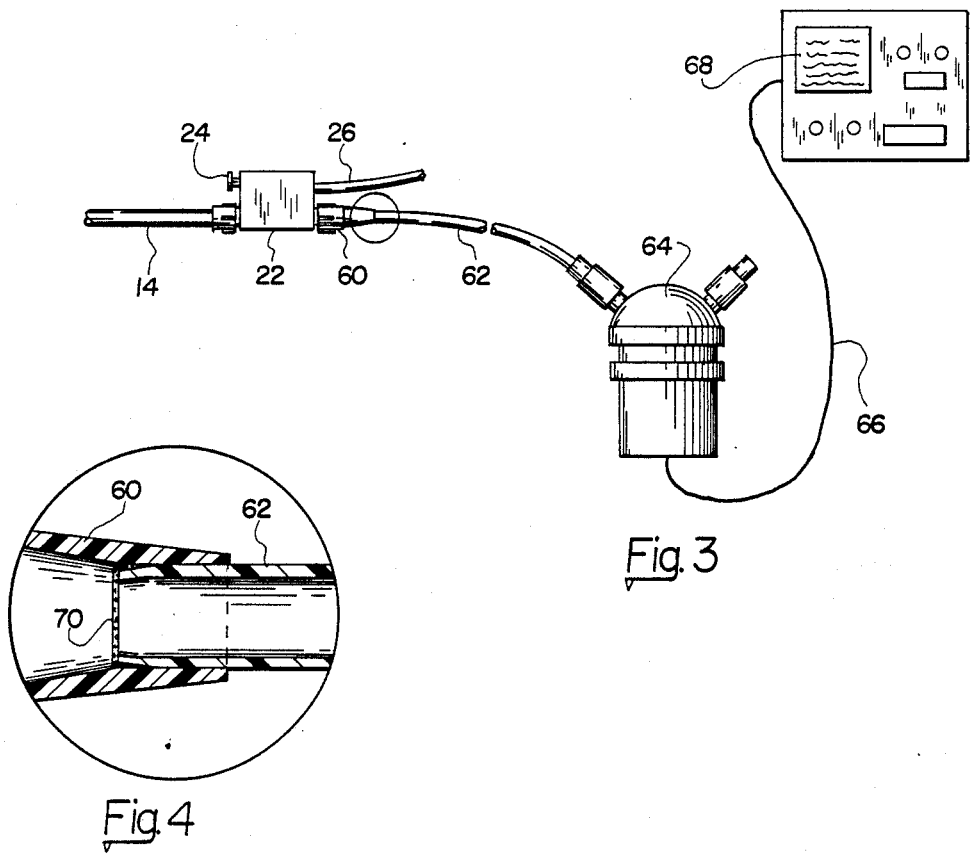
Fig. 3
Fig. 4
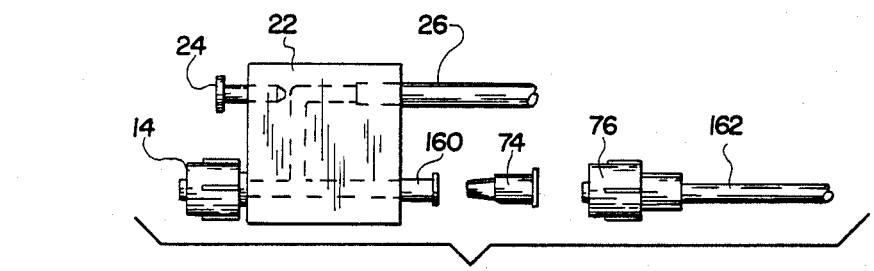
Fig. 5A
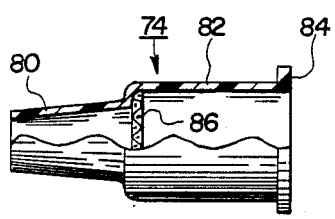
Fig. 5B

BLOCKING FILTER TO PREVENT AIR FLOW INTO A FLUID CONDUIT TO A TRANSDUCER

BACKGROUND OF THE INVENTION

1. Field of the Invention

This invention pertains to blood pressure monitoring apparatus employing a catheter placed in the artery. The pressure in the artery may be displayed as a waveform, digital readout, or permanently recorded on a strip chart at a monitor. This apparatus is found in the general class of SURGERY. This invention shows a tube system from a supply system for automatically preventing the presence of unwanted air bubbles from the catheter to a monitor. This air may intially develop in the connectors or tubing connected to the supply tube leading to the catheter. The present device uses a filter to block air from the supply system to the pressure transducer.

2. Description of the Prior Art

Physiological pressure measuring and monitoring of arterial blood has been used for many years. This procedure uses a catheter whose end is inserted into an artery of the patient. This catheter, with support tubing, stopcocks, continuous flush device, domes, etc., connects the arterial blood with a pressure signal transducer through a fluid path. The transducer converts the hydraulic pressure into electrical signals which are sent to the monitor. The monitor converts these signals into visual waveforms, numerical values and/or permanent records using strip charts. The fluid path for conducting hydraulic pressure signals is continuous from the catheter to a diaphragm within the dome of the transducer. This diaphragm, which is a portion of the transducer, is physically responsive to the hydraulic pressure and its variations within the fluid system. The transducer is able to detect these pressures and their variations through the diaphragm and transmit them in electrical form to the monitor.

When an artery of a patient is "invaded," the natural defense mechanism for preventing infection is violated. Hence, it becomes extremely important that the entire blood pressure monitoring system be initially sterile and their sterility maintained during the procedure. This includes all fluid connections, surfaces and components in contact with the blood system.

Many symposiums, conferences, papers and articles have been directed toward problems of less than satisfactory waveforms or results. A primary factor contributing to less than satisfactory results is overdamping, which is caused primarily by air bubbles in the system. Blood or thrombii left in the catheter following blood sampling may also contribute to overdamping. Air bubbles are also a major cause of lowering the resonant frequency of the system which, in turn, causes ringing or wave amplitude distortion. The size as well as location of air bubbles is significant with respect to their effect on the waveform. With a given size, an air bubble when close to the transducer in the tubing system may result in a lowering of the resonant frequency from ten to twenty Hertz.

As noted above, the compressible nature of air bubbles in the fluid conductor also diminishes and otherwise degrades the hydraulic signal to the diaphragm of the pressure tranducer. Trandsucers have been known, for example from U.S. Pat. Nos. 2,841,984; 4,072,056 and 4,252,126. These last two patents were directed to use in the recording of hemodynamic pressure in an artery. Of particular note is U.S. Pat. No. 4,365,635 which shows a special dome construction for removing entrapped air. A major problem associated with that system is that it does not provide for elimination of air once the transducer has been hooked up to the dome.

U.S. Pat. No. 4,252,126 describes a transducer dome in which the filter or diaphragm is carried so that any accumulation of bubbles after the unit has been brought to operating condition is not vented.

The present apparatus provides a supply of fluid from a bag supply through a flexible tube leading from this supply. This tube may include a flushing device, one or more entry cocks which are adapted for adding of drugs in liquid form, and connection to a catheter which is placed in a patient. In one embodiment, this infeed line is flow-connected to a second tube conductor which carries the pressure variations through this fluid to the pressure transducer. At the entrance to this second line, an in-line hydrophilic filter prevents any air to flow into the second line and pressure transducer. The positive elimination of air bubbles in the second line to the pressure transducer is not shown in prior art above or known to the Applicant.

In an alternate embodiment, an in-line hydrophilic filter is provided at the fast-flushing device and this filter is before and in way of a conducting fluid line which is filled with fluid and purged so that this fluid line leads to a transducer. This alternate device is specifically adapted to be used with present blood pressure appparatus so as to provide an air-free conductor.

SUMMARY OF THE INVENTION

This invention may be summarized, at least in part, with reference to its objects. It is an object of this invention to provide, and it does provide, a two-lumen tube system with a filter secured at the end of one tube member to positively prevent air bubbles from entering said tube and having the fluid conducted to a transducer.

It is a further object of this invention to provide, and it does provide, a two-lumen tube apparatus in which a catheter is provided with a hub portion which is flow-connected to each tube portion and the tube leading from the fluid-supply bag or source to the catheter is provided with flushing means and the like to provide continuous fluid flow and means for accessing the system, and at the inlet end of the second tube there is disposed an inline hydrophilic screen filter which prevents any and all air "bubbles" from passing into the fluid in this tube to a connected pressure transducer.

It is a further object of this invention to provide, and it does provide, an in-line hydrophilic filter that is connected to a tubular conductor having one end connected to the fast-flush device and the other end to a pressure transducer. This pressure transducer and conductor are disposed to send electrical signals to a monitor with or without recording capability.

The accurate measurement of blood pressure depends on the ability of the fluid-filled catheter's system to faithfully transmit the residual pressure, which varies with the cardiac cycle. In the embodiment to be shown and described, it is contemplated that the filter membrane is supported by a reinforcement such as a nonwoven substrate. However, it may be unsupported if due care is exercised during the liquid filling of the tubing.

Frequency response is a term used to express the faithfulness of a system to reproduce "what is occurring." The concept of frequency response can be considered as follows: Any signal or waveform that is periodic, including pulsatile waveforms, can be electronically resolved into a series of signals of various frequencies. Each of these frequency components is a multiple of a fundamental frequency and is characterized by a maximum amplitude. The plumbing system must be capable of faithfully transmitting each of the necessary frequency components of a pressure wave without distorting the amplitude.

Distortion of any of these frequency components can result in pressure values that are falsely high or falsely low depending on the type of distortion. The ability or inability of a system to faithfully transmit each of these frequency components of a signal without distortion of the amplitude is defined to be the frequency responsiveness (or response) of that system. The responsiveness in turn of a catheter plumbing system depends upon the resonant frequency of that system and whether or not the system is overdamped or underdamped.

In prior devices, the attention has been directed toward minimizing air "bubbles" in the tube carrying signals to a pressure transducer. Conventionally, this has been a single fluid-conducting flexible tube to a transducer dome and venting of said "bubbles" is from the dome. In such systems, the responsiveness of a pressure-monitoring system is determined by length and diameter of the catheter and tubing as well as the stiffness of the materials, the type and number of stopcocks, valves and other pieces of hardware, and the amount of air that is trapped in the system. Given that a catheter plumbing system has a resonant frequency, determined by the above, if the pressure wave being transmitted through this system contains a component whose frequency equals the resonant frequency of the system, then the system will tend to vibrate. The resonation of the plumbing system with this frequency component of the pressure waveform may exhibit itself as an overshoot of the systolic portion of the waveform followed by "ringing" as characterized by small oscillations seen on the waveform after systole. When detected by a pressure monitor, this ringing may result in high systolic readings. If the reading is severe enough, one will see a negative going excursion of the pressure waveform which would result in low diastolic values. This accentuation of the pressure waveform is often observed with pressure waves having a high rate of pressure increase (dp/dt) occurring during systole. In constructing the catheter plumbing system, it is desirable to have its inherent resonant or characteristic frequency be as far removed as possible from the frequency values of the signal being transmitted. In this way, "ringing" is precluded. Normally, the typically designed pressure-monitoring system often results in a resonant frequency which is greater than any of the frequencies being monitored. The major operating problem is the introduction and/or trapping of air within the pressure-monitoring system.

In the invention to be shown and described hereinfafter, a comparison is made with a conventional pressure transducer and monitor system. The placing of a screen filter at the inlet of a fluid conductor to a pressure transducer does not significantly affect the resonant frequency properties of the system. For example, in a carefully conducted series of experiments, a "standard" system was found to resonate at 34 Hertz. A screen filter as in the present invention was introduced and the resonant frequency changed to 32 Hertz. This value is more than satisfactory for invasive blood pressure monitoring uses.

There are shown two embodiments of filter system to prevent "bubbles" of air or the like from entering the fluid conductor to the pressure transducer. In a first embodiment, a two-lumen tube system with an interposed filter is provided and, although intended primarily for blood pressure monitoring, may be used in other systems where "bubble" presence is very detrimental. From a continuous-flush device, fluid is fed through a flexible conducting tube to a catheter connecting hub. At this connecting hub there is provided a second tube whose inlet end is provided with an inline hydrophilic screen filter, with this flexible tube extending to a monitor and stopcock. This second tube conductor is filled with fluid and, when purged, is absent any "air bubbles" and is maintained in this condition by the filter screen.

The two-lumen tube system is shown in the drawings and is described hereafter. After initially priming the system to fill the lines with fluid and purge any air that may be present in the pressure transducer line, the system is attached to a catheter which has been inserted previously into the patient. When any of the stopcocks are opened and air bubbles enter the system, they are prevented from entering the pressure transducer line by the in-line hydrophilic screen filter. It has been found that bubbles that were deliberately introduced into the system and allowed to accumulate at the screen filter had almost a negligible effect on the resonant frequency of the pressure transducer line. Also, any dissolved air in the line was prevented from entering the pressure transducer line by the filter. Filters having ratings of 10 micron through 0.2 micron exhibited quite similar properties with regard to hydrodynamic response characteristics. The 0.2 micron filter has the added benefit of preventing bacteria which may enter the pressure transducer line from entering the patient.

An alternate embodiment provides a blocking filter in an added device mounted in a fast-flushing device as conventionally provided in a blood pressure monitor and recorder. This blocking filter provides a connecting means to a fluid conductor to a pressure transducer. Although a small amount of pulse pressure wave amplitude may be lost, the resulting waveform is a true reflection of the pulses in the patient.

In addition to the above summary, the following disclosure is detailed to insure adequacy and aid in understanding of the invention. This disclosure, however, is not intended to cover each new inventive concept no matter how it may later be disguised by variations in form or additions of further improvements. For this reason, there have been chosen specific embodiments of the blocking filter to prevent air flow into a fluid conduit as adopted for use with a pressure transducer and the like and showing a preferred means for assembling and using said system. These specific embodiments have been chosen for the purposes of illustration and description as shown in the accompanying drawings wherein:

BRIEF DESCRIPTION OF THE DRAWINGS

FIG. 1 represents a plan and diagrammatic view of a two-lumen tube system having an air-blocking filter mounted in a connector hub as used in the two-lumen delivery system;

FIGS. 2 A, 2 B and 2 C represent securement arrangements of the filter screen at the entrance end of the second tube leading to the pressure tansducer;

FIG. 2 A represents in an enlarged, diagrammatic sectional side view a first arrangement of securing the filter screen to the end of a fluid-conducting tube;

FIG. 2B represents an alternate arrangement of securing the filter to the end of the tube, this view substantially like the enlarged sectional view of FIG. 2 A;

FIG. 2 C represents yet another alternate arrangement essentially like the enlarged view of FIG. 2 A, but showing this further alternate filter screen securement;

FIG. 3 represents a plan view of the present arrangement of a blood-pressure recording system, but utilizing the fast-flush device to connect by an alternate route a fluid conductor which has a filter screen at the entrance end of said conductor;

FIG. 4 represents a fragmentary, sectional side view of the tubular conductor with mounted and secured filter screen;

FIG. 5 A represents a side view, partly diagrammatic, and exploded to illustrate the relationship of the several components, and FIG. 5 B represents in a fragmentary and enlarged scale the filter connector device utilized in FIG. 5 A.

In the following description and in the claims, various details are identified by specific names for convenience. These names are intended to be generic in their application. Corresponding reference characters refer to like members throughout the several figures of the drawings.

The drawings accompanying, and forming part of, this specification disclose details of construction for the purpose of explanation, but structural details may be modified without departure from the concept and principles of the invention and the invention may be incorporated in other structural forms than shown.

DESCRIPTION OF EMBODIMENT OF FIG. 1

Referring next to the drawings and a two-lumen tube system with filter, there is depicted in FIG. 1 a schematic line drawing diagrammatically showing a system employing a preferred arrangement for transmitting resonant frequencies to a monitor. A catheter 10 has a hub portion 12 of a selected configuration. The two-lumen tube system is shown mounted and connected to this hub. A first tube 14 is selectively provided with stopcocks 16, 17 and 18 which are conventional and provide means for obtaining blood samples, injection of medication, etc. The proximal end of tube 14 is shown with a connector end 20 which is adapted to be removably attached to a continuous flushing device, generally identified as 22. This device is conventional and provides a continuous influent delivery of fluid through the tube 14. The tubing 14 is compliant (flexible) but substantially nonelastic, and is usually of plastic such as Tygon (Trademark of Norton Co.).

The continuous-flushing device 22 has a fast-flush button 24 which, when actuated, allows fluid from a connection 26 to flow from a supply of fluid such as a bag (not shown) to enter line 14 at a high rate of flow and thereby fill up this line and flush air and other debris from this line in a very short period of time (seconds). This continuous-flush device has a restrictor element (conventional) which controls the rate of normal fluid flow to one to five cc./hr. Although the restricted rate of fluid flow from the bag through the flushing device is from one to five cc's per hour, the "fast flush" actuated by button 24 produces a fast fluid flow of about one hundred twenty-five to one hundred seventy-five cc's per minute. This rapid flow allows the connected system to be filled rapidly with fluid in about five seconds. Also shown as extending from the continuous-flush device 22 is a stopcock 28 which is removably connected to the other inlet of the device. This stopcock 28 may be used as desired for example when fluid-flow delivery from the connection 26 is shut off.

The hub 12 may be a molding specifically adapted to receive and retain the end portions of the two-lumen tubes 14,30. There are many arrangements within the selection of the designer and/or engineer for securing the distal ends of the dual-tube arrangement. A cavity 32 provides a communication chamber for fluid flow and intermingling of the fluid from tube 14 to and into tube 30. The rear portion 34 of this hub or housing, is sized to receive and retain a screen filter 36 which is adapted to cover the end of the tubing 30. The tubing 30 extends to a connector 38 and a T-fitting 40. The fitting 40 is adapted to have extending at the midportion thereof a connection and/or conductor tube 42 to a monitor 43. A removable connection and a stopcock 44 are also shown as secured to the T-connector 40. The tubes 30, 42 are made as IV tubing similar to that of tube 14 described above.

EMBODIMENT OF FIGS. 2 A, 2 B AND 2 C

The enlarged view of FIG. 2 A depicts the arrangement of the filter screen 36 at the end of tube 30. This filter, whether a layered filter with a support or as a structured screen material, is hydrophilic. The attachment to the end of the tube 30 is adapted so that only fluid can pass from the cavity 32 into the tube 30. Fixed securing may be achieved by heat, solvent, cement, friction or combinations thereof. Sonic welding is also known as a method of and for attachment. As shown in this sectional side view, the filter screen 36 is formed with a cup-shape that is a press or a cemented fit in the passageway provided for tube 30. Tube 30 is shown as of plastic and is sufficiently flexible to be inserted into and within the interior of filter screen 36.

In FIG. 2 B the showing is very like the structure of FIG. 2 A but, rather than with a cup-shape, this screen filter (identified as 136) is a disc-like member that is secured in position in the aperture provided for tubular member 30. This aperture is formed in the housing 34 and the securing of this filter screen may be to the end of this tubing 30 or in the aperture. It is noted that the positioning of this filter screen in way of the exit end of tubing 14 is also contemplated, but the intent of preventing any and all air from entering tubular conductor 30 is essential.

In FIG. 2 C the embodiment of FIG. 2 A is repeated but, rather than securing the filter screen as above, the screen filter (identified as 236) is similar to that in FIG. 2 A in that it is made cup-shaped but is also mounted on and secured to an end ring 50. This filter screen 236 may be secured to this ring 50 either by friction or cement or the like. The ring 50 may be a press fit within the molded aperture for tube 30 or may be secured by adhesive or the like. This ring 50 may or may not be attached to the end of tube 30.

It is to be noted in FIGS. 2 A, 2 B and 2 C that the arrangement of the filter screen is at the entrance of and to fluid-conducting tube 30 which carries the signal to the transducer and/or monitor 43. This filter screen prevents air or bubbles from entering fluid-filled tube 30 during the reading of pulses.

EMBODIMENT OF FIG. 3

In FIG. 3 is diagrammatically depicted the conventional bloodpressure monitoring device now used in hospitals. From a bag (not shown), fluid is delivered through a tubular conductor 26 to a fast-flush device 22 as described above. The button 24 releases fluid in a fast flow through connector 20 to tubing 14. The exit port from fast-flush device 22 rather than to stopcock 28 is now to a connector 60 and a tubular conductor 62. This conductor 62 in this view if connected to a transducer dome 64. This dome is provided with electrical conductors 66 leading from the transducer to a monitor-recorder 68. The transducer and monitor are very conventional.

EMBODIMENT OF FIG. 4

In FIG. 4, in a fragmentary and greatly enlarged side view, is shown the connector 60 with conductor 62 secured thereto. A filter screen 70 is shown as having a cup-shape and is disposed to provide an exclusion capability to the passage of air while passing fluid and particularly signal pulses in said fluid. This filter screen 70 and conductor 62 are secured as by adhesive, welding and the like to prevent unwanted disassembly and any possible leakage.

EMBODIMENT OF FIGS. 5 A AND 5 B

Referring next, and finally, to the drawings, there is depicted in FIGS. 5 A and 5 B an alternate arrangement of providing a filter screen in way of a fluid conductor. In this embodiment, the fast-flush device 2 is still utilized. An infeeding tubular conductor 14 carries a solution from a supply bag, not shown. An outlet conductor 160 is provided, and connected thereto and mounted therein is a filter screen connector 74. A filter screen connector member 76 is adapted to be mounted to a larger end of filter screen connector 74. A tubular conductor 162 is secured to connector member 76.

In FIG. 5 B the connector 74 is depicted as a shell molding in which a tapered forward end 80 extends to a larger diameter tubular portion 82 and terminates at the right end with a connecting flange portion 84. Interior of the tubular portion 82 is a filter screen disc 86 which is secured to the left face of the transition from taper 80 to tubular portion 82. This securement may be by adhesive, welding or a force fit. It is desired that the filter 86 exclude flow around the periphery or that any leakage does not occur as the filter screen 86, like those described above, is to allow flow of fluid while excluding any and all air or gas.

USE AND OPERATION OF EMBODIMENT OF FIGS. 3 THROUGH 5 B

In the showing of FIGS. 3 through 5 B, it is anticipated that this filter screen be used in and with apparatus currently and conventionally used in hospitals, doctors' offices and the like. Rather than carry fluid from a supply to the catheter hub, the fluid path is from tubular member 14 through fast-flush device 22, which is conventional, and then to and through the filter screen and thence through conductor or tube 62 or 162 to the transducer dome. This filter screen is interposed in this line so that pulse readings are more accurate as any air present is found in line 14 and distortion of said pulse signals is drastically reduced as the fluid-conducting tube 62 is absent any air or gas bubbles. The reduction in frequency response characteristics may be from the "nominal" thirty to thirty-four Hertz down to frequencies in the twenty to twenty-five Hertz range. This reduction may occur when air bubbles are present in the system at the filter fluid interface. However, this frequency reduction still allows the practitioner to accurately interpret the waveform and make clinical judgment concerning vital functions relating to the patient's blood pressure.

The above blocking filter in its assembly and use suggests and teaches a method of securing and positioning a blocking filter so as to prevent air and the like to flow into a fluid conduit leading to a transducer, said filter being hydrophilic so as to exclude the passage therethrough of air while passing fluids, and disposing this filter so as to be in way of a fluid conductor of pulse signals from a patient to a transducer, said method including the steps of:

providing a fluid-conducting member of flexible tubing and connecting a first end to a supply source and a second end to a fast-flush device having control means to selectively increase the fluid flow so as to purge said conductor of bubbles of air, gas and the like;

positioning a blocking filter of hydrophilic material in way of the fluid flow through a tubular conductor leading from the fast-flush device to a transducer, and constructing said filter so that when in use said filter excludes any and all air, gas and like bubbles in said fluid conductor so that pulse signals sent through said conductor from a patient to the transducer and through that conductor connected to the transducer are not distorted by the presence of bubbles, and expelling the bubbles in said inflow fluid conductor before the measuring of pulses from the patient.

The blocking filter is shown in two embodiments and is particularly directed to blood-produced signals sent through a fluid line to a transducer. In describing the components and their relationship, terms such as "left," "right," "up," "down," "bottom," "top," "front," "back," "in," "out" and the like are applicable to the embodiments shown and described in conjunction with the drawings. These terms are merely for the purposes of description and do not necessarily apply to the position in which the blocking filter may be constructed or used.

What is claimed is:

1. A system for transmitting resonant frequencies to a monitor comprising
    a hub for connection to a catheter at a distal end;
    a first tube connected to a proximal end of said hub for conveying fluids therebetween;
    a second tube connected to said proximal end of said hub for conveying a fluid from said hub to an arterial blood pressure measuring monitor; and
    a hydrophilic filter at a distal end of said second tube and within said hub for preventing passage of air bubbles from said hub and said first tube into said second tube.

2. A system as set forth in claim 1 which further comprises a continuous-flushing device connected to said first tube for flushing air from said first tube.

3. A system as set forth in claim 1 wherein said hub has a common cavity receiving said tubes therein.

4. A system as set forth in claim 1 which further comprises at least one stopcock in said first tube for administration of drugs.

5. In combination,
    a catheter for insertion at a distal end into an artery, said catheter having a hub at a proximal end;

a first tube connected to a proximal end of said hub for conveying fluids therebetween;

a second tube connected to said proximal end of said hub for conveying a fluid from said hub;

a hydrophilic filter at a distal end of said second tube and within said hub for preventing passage of air bubbles from said hub and said first tube into said second tube; and an arterial blood pressure measuring monitor connected to said second tube for receiving blood pulse signals therefrom.

6. A system as set forth in claim 5 which further comprises a continuous-flushing device connected to said first tube for flushing air from said first tube.

7. A system as set forth in claim 5 wherein said hub has a common cavity receiving said tubes therein.

8. A system as set forth in claim 5 which further comprises at least one stepcock in said first tube for administration of drugs.

9. In combination, a catheter for insertion at a distal end into an artery;

a first tube connected to and extending from said catheter;

a fast-flush device connected to a proximal end of said first tube;

a second tube connected to said fast-flush device for delivering fluid thereto for flushing of said first tube;

a third tube connected to said fast-flush device for receiving a flow of arterial flood from said first tube;

a hydrophilic filter at a distal end of said third tube for preventing passage of air bubbles from said device into said third tube;

a transducer dome connected to said third tube to convert hydraulic pressure of the arterial blood into electrical signals; and a monitor-recorder connected to said dome to receive and record said electrical signals.

* * * * *

UNITED STATES PATENT AND TRADEMARK OFFICE
CERTIFICATE OF CORRECTION

PATENT NO.  : 4,834,108
DATED       : May 30, 1989
INVENTOR(S) : VINCENT L. VAILLANCOURT

It is certified that error appears in the above-identified patent and that said Letters Patent is hereby corrected as shown below:

```
Column 1, line 44  "their" should be -this-
Column 2, line 48  "inline" should be -in line-
Column 6, line 16  "tubing" (both occurrences) should be -tube-
Column 7, line 11  "if" should be -is-
Column 10, line 10 "flood" should be -blood-
```

Signed and Sealed this

Eighth Day of May, 1990

Attest:

HARRY F. MANBECK, JR.

Attesting Officer

Commissioner of Patents and Trademarks